(12) United States Patent
Nam et al.

(10) Patent No.: US 11,925,438 B2
(45) Date of Patent: Mar. 12, 2024

(54) APPARATUS AND METHOD FOR ESTIMATING BODY TEMPERATURE, AND HEALTHCARE DEVICE

(71) Applicant: SAMSUNG ELECTRONICS CO., LTD., Suwon-si (KR)

(72) Inventors: Sung Hyun Nam, Yongin-si (KR); So Young Lee, Daejeon (KR); Ka Ram Choi, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/967,541

(22) Filed: Oct. 17, 2022

(65) Prior Publication Data

US 2023/0034618 A1 Feb. 2, 2023

Related U.S. Application Data

(62) Division of application No. 17/217,481, filed on Mar. 30, 2021, now Pat. No. 11,717,171.

(30) Foreign Application Priority Data

Nov. 23, 2020 (KR) ........................ 10-2020-0157717

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/0075* (2013.01); *A61B 5/021* (2013.01); *A61B 5/0537* (2013.01);
(Continued)

(58) Field of Classification Search
CPC ......... A61B 5/01; A61B 5/0075; A61B 5/021; A61B 5/0537; A61B 5/14532;
(Continued)

(56) References Cited

U.S. PATENT DOCUMENTS 7,460,895 B2    12/2008    Arnold et al.
7,734,321 B2    6/2010    White
(Continued)

FOREIGN PATENT DOCUMENTS

JP    5964773 B2    8/2016
JP    2018-21833 A    2/2018
(Continued)

OTHER PUBLICATIONS

U.S. Appl. No. 17/119,634, filed Dec. 11, 2020, Choi et al.
(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for estimating body temperature of an object is provided. The apparatus for estimating body temperature includes: a sensor configured to obtain spectra through a plurality of light paths of an object; and a processor configured to obtain a temperature slope between temperatures corresponding to the plurality of light paths based on the spectra of the plurality of light paths and a reference spectrum measured at a reference temperature, and estimate the body temperature of the object based on the temperature slope.

4 Claims, 11 Drawing Sheets

(51) Int. Cl.
  *A61B 5/021* (2006.01)
  *A61B 5/0537* (2021.01)
  *A61B 5/145* (2006.01)
  *A61B 5/16* (2006.01)
  *G01K 13/20* (2021.01)

(52) U.S. Cl.
  CPC .......... *A61B 5/14532* (2013.01); *A61B 5/165* (2013.01); *A61B 5/442* (2013.01); *A61B 5/4872* (2013.01); *A61B 5/6803* (2013.01); *A61B 5/681* (2013.01); *A61B 5/6833* (2013.01); *A61B 5/6898* (2013.01); *G01K 13/20* (2021.01); *A61B 2562/0271* (2013.01)

(58) Field of Classification Search
  CPC ....... A61B 5/165; A61B 5/442; A61B 5/4872; A61B 5/6803; A61B 5/681; A61B 5/6833; A61B 5/6898; A61B 2562/0271; A61B 5/14546; A61B 5/4875; A61B 5/7264; A61B 5/6802; A61B 5/7275; A61B 2560/0247; G01K 7/42; G01K 7/427; G01K 11/12; G01K 13/20; G01K 11/006
  See application file for complete search history.

(56) References Cited

U.S. PATENT DOCUMENTS

| | | | |
|---|---|---|---|
| 7,873,397 | B2 | 1/2011 | Higgins et al. |
| 10,206,577 | B2 | 2/2019 | Jang et al. |
| 10,506,989 | B2 | 12/2019 | Maruo |
| 10,753,797 | B2 | 8/2020 | Kim et al. |
| 2005/0203358 | A1 | 9/2005 | Monfre et al. |
| 2007/0084990 | A1 | 4/2007 | Coates |
| 2010/0160750 | A1 | 6/2010 | White et al. |
| 2010/0249546 | A1 | 9/2010 | White |
| 2011/0108730 | A1* | 5/2011 | Herrmann .................. G01J 5/58 250/339.04 |
| 2016/0103063 | A1 | 4/2016 | Kurasawa et al. |
| 2017/0319066 | A1 | 11/2017 | Ver Steeg et al. |
| 2018/0146899 | A1 | 5/2018 | Lee et al. |
| 2018/0188117 | A1 | 7/2018 | Matousek et al. |
| 2018/0232581 | A1 | 8/2018 | Reinpoldt et al. |
| 2019/0117136 | A1 | 4/2019 | Lee et al. |
| 2019/0154656 | A1 | 5/2019 | Bae et al. |
| 2019/0159680 | A1 | 5/2019 | Tanaka et al. |
| 2019/0313914 | A1 | 10/2019 | Kirenko et al. |
| 2020/0037884 | A1 | 2/2020 | Ishida et al. |
| 2020/0107759 | A1 | 4/2020 | Lee |
| 2020/0121244 | A1 | 4/2020 | Lee et al. |

FOREIGN PATENT DOCUMENTS

| | | |
|---|---|---|
| JP | 2019-531825 A | 11/2019 |
| KR | 10-2010-0054131 A | 5/2010 |
| KR | 10-2019-0057743 A | 5/2019 |
| KR | 10-2020-0009869 A | 1/2020 |

OTHER PUBLICATIONS

Co-pending U.S. Appl. No. 17/119,634, filed Dec. 11, 2020, Choi et al.

Chamathca P.S. Kuda-Malwathumullage et al., "Temperature correction strategy for improving concentration predictions with near-infrared spectra of aqueous-based samples", Analytica Chimica Acta 1095, Sep. 14, 2019, pp. 20-29 (10 pages total).

Communication dated Jan. 24, 2022 by the European Patent Office in counterpart European Patent Application No. 21190304.2.

Gunga et al., "A non-invasive device to continuously determine heat strain in humans," Elsevier, Journal of Thermal Biology, vol. 33, pp. 297-307, 2008, Total 12 pages.

Peter Snoer Jensen et al., "Influence of Temperature on Water and Aqueous Gluclose Absorption Spectra in the Near- and Mid-Infrared Regions at Physiologically Relevant Temperatures", Applied Spectroscopy, Aug. 24, 2002, vol. 57, No. 1, pp. 28-36 (9 pages total).

\* cited by examiner

APPARATUS AND METHOD FOR ESTIMATING BODY TEMPERATURE, AND HEALTHCARE DEVICE

CROSS-REFERENCE TO RELATED APPLICATION(S)

This application is a divisional of U.S. application Ser. No. 17/217,481 filed Mar. 30, 2021, which claims priority from Korean Patent Application No. 10-2020-0157717, filed on Nov. 23, 2020 in the Korean Intellectual Property Office, the disclosures of which are incorporated herein by reference in their entirety

BACKGROUND

1. Field

Apparatuses and methods consistent with example embodiments relate to estimating body temperature by using an optical sensor.

2. Description of the Related Art

Generally, body temperature is one of the four main vital signs and has very important clinical significance. A body temperature sensor may be used in various applications, such as checking infections in patients, thermal side effects of medications, or time of ovulation in women, and the like. However, the skin temperature and deep body temperature may vary depending on external temperature, such that it is difficult to measure the deep body temperature by using a portable device such as a wearable device. A general body temperature sensor may be classified into a contact type sensor and a non-contact type sensor. Examples of the contact type sensor may include a sensor for detecting a change in electrical resistance, such as a Resistance Temperature Detector (RTD), a thermistor, etc., a thermocouple for detecting electromotive force, and the like. Further, examples of the non-contact type sensor may include a thermopile, a micro-bolometer, and the like, which measure body temperature by detecting infrared rays radiating from a body surface. A general body temperature measuring technology is affected significantly by a change in environment factors affecting heat transfer, such as a change in external ambient temperature, humidity, air flow, and the like.

SUMMARY

According to an aspect of an example embodiment, there is provided an apparatus for estimating body temperature, the apparatus including: a sensor configured to obtain spectra through a plurality of light paths of an object; and a processor configured to obtain a temperature slope between temperatures corresponding to the plurality of light paths based on the spectra of the plurality of light paths and a reference spectrum measured at a reference temperature, and estimate the body temperature of the object based on the temperature slope.

The reference spectrum may be measured by using a light in a water absorption wavelength range.

The sensor may include: a light source configured to emit light onto the object; and a detector configured to detect the light scattered or reflected from the object after the light is emitted by the light source.

At least one of the plurality of light paths may penetrate into a depth of dermis or another depth deeper than the depth of dermis.

The processor may be further configured to normalize the spectra of the plurality of light paths, respectively, based on the reference spectrum, and obtain the temperature slope based on the normalized spectra of the plurality of light paths.

The processor may be further configured to estimate a mean temperature of the respective plurality of light paths based on a difference between the reference spectrum and the respective spectra of the plurality of light paths, and obtain the temperature slope based on the estimated mean temperature.

The processor may be further configured to estimate the body temperature of the object based on the reference temperature and the temperature slope by using a body temperature estimation equation.

The processor may be further configured to: estimate a mean temperature of a reference path selected from the plurality of light paths; and estimate the body temperature of the object based on the temperature slope and the mean temperature of the reference path by using the body temperature estimation equation.

The processor may be further configured to determine a shortest light path among the plurality of light paths as the reference path.

The apparatus may further include an output interface configured to output the estimated body temperature of the object.

According to an aspect of another example embodiment, there is provided a healthcare device including: a main body including the apparatus for estimating the body temperature; a display mounted on the main body, wherein the processor may be further configured to perform at least one of a first mode of estimating the body temperature of the object, a second mode of estimating bio-information based on the obtained spectra, and a third mode of estimating the body temperature and the bio-information, and control the display to display a result of performing at least one of the first mode, the second mode, and the third mode.

According to an aspect of another example embodiment, there is provided an apparatus for estimating body temperature, including: a spectrometer configured to obtain a spectrum through a light path passing through a tissue underneath a surface of an object; a temperature sensor configured to measure a surface temperature from the surface of the object; and a processor configured to obtain a temperature slope between a temperature corresponding to the obtained spectrum and the surface temperature, based on the obtained spectrum and a reference spectrum corresponding to the surface temperature, and estimate the body temperature of the object based on the temperature slope.

The processor may be further configured to normalize the spectrum obtained through the light path based on a reference spectrum corresponding to the surface temperature, and obtain the temperature slope based on the normalized spectrum.

The processor may be further configured to estimate a mean temperature of the light path based on a difference between the reference spectrum and the normalized spectrum, and obtain the temperature slope based on the surface temperature and the mean temperature.

The processor may be further configured to estimate the body temperature of the object based on the surface temperature and the temperature slope by using a body temperature estimation equation.

According to an aspect of another example embodiment, there is provided a method of estimating body temperature, including: obtaining spectra through a plurality of light paths of an object; obtaining a temperature slope between temperatures corresponding to the plurality of light paths based on the spectra of the plurality of light paths and a reference spectrum measured at a reference temperature; and estimating the body temperature of the object based on the temperature slope.

The obtaining the temperature slope may include normalizing the spectra of the plurality of light paths, respectively, based on the reference spectrum, and obtaining the temperature slope based on the normalized spectra of the plurality of light paths.

The obtaining the temperature slope may include estimating a mean temperature of the plurality of light paths based on a difference between the reference spectrum and the normalized spectra of the plurality of light paths, and obtaining the temperature slope based on the estimated mean temperature.

The estimating the body temperature may include estimating the body temperature of the object based on the reference temperature and the temperature slope by using a body temperature estimation equation.

The estimating the body temperature may include: estimating a mean temperature of a reference path selected from the plurality of light paths; and estimating the body temperature of the object based on the temperature slope and the mean temperature of the reference path.

The obtaining the spectra may include obtaining a first spectrum through a first light path passing through a tissue underneath a skin surface of an object, the method may further include measuring, as the reference temperature, a surface temperature from the skin surface of the object; the obtaining the temperature slope may include obtaining a first temperature slope between a first temperature corresponding to the first spectrum and the surface temperature, based on the obtained spectrum and a reference spectrum corresponding to the surface temperature; and the estimating the body temperature may include estimating the body temperature of the object based on the first temperature slope and the surface temperature.

According to an aspect of another example embodiment, there is provided a method of estimating body temperature, the method including: obtaining a spectrum in a light path passing through a deep portion of an object; measuring a surface temperature from a surface of the object; obtaining a temperature slope based on the obtained spectrum and a reference spectrum corresponding to the surface temperature; and estimating body temperature of the object based on the obtained temperature slope and the surface temperature.

According to an aspect of another example embodiment, there is provided a healthcare device, including a main body; a sensor mounted on the main body and configured to obtain a spectrum from an object; a display mounted on the main body; and a processor configured to perform at least one of a first mode of estimating body temperature of the object by obtaining a temperature slope based on the obtained spectrum and a reference spectrum, a second mode of estimating bio-information based on the obtained spectrum, and a third mode of estimating the body temperature and the bio-information, and to display a result of the estimation on the display.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
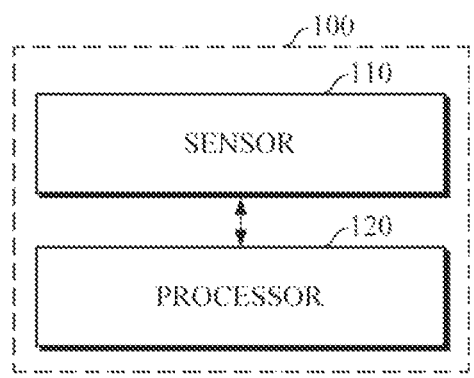
FIG. 1 is a block diagram illustrating an apparatus for estimating body temperature according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Figure 2A:
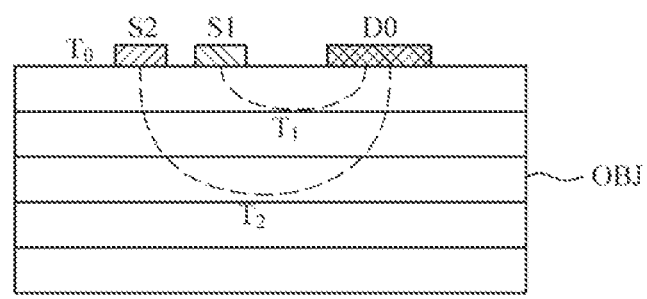
FIGS. 2A and 2B are diagrams illustrating a configuration of a sensor according to the example embodiment of FIG. 1.
Figure 2B:
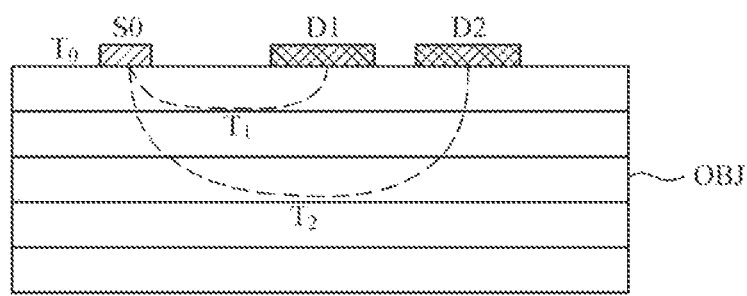
Figure 2C:
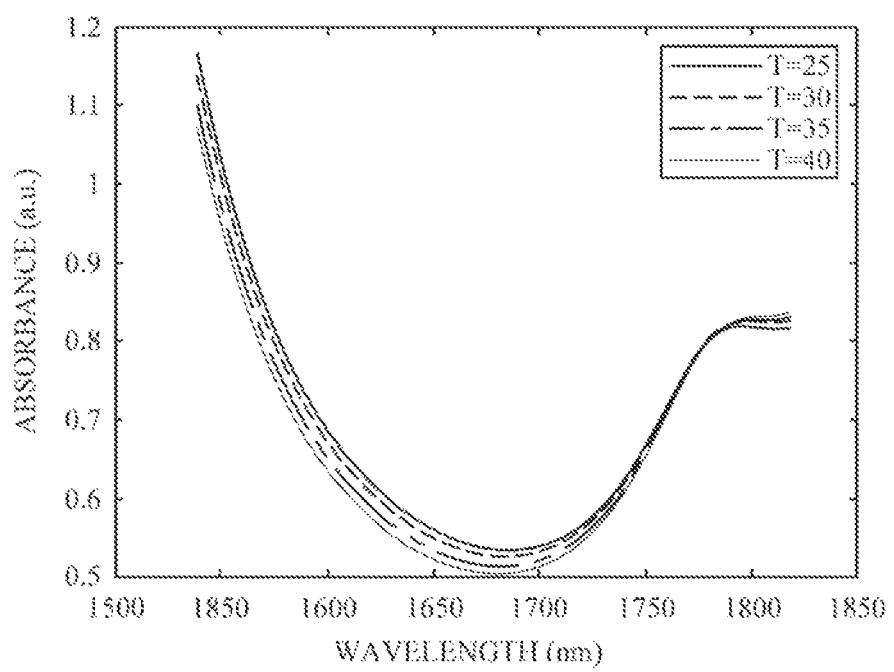
FIG. 2C is a diagram illustrating a change in water absorption spectrum according to a temperature change.

FIG. 1 is a block diagram illustrating an apparatus for estimating body temperature according to an example embodiment. FIGS. 2A and 2B are diagrams illustrating a configuration of a sensor according to the embodiment of FIG. 1. FIG. 2C is a diagram illustrating a change in water absorption spectrum according to a temperature change.

Referring to FIG. 1, an apparatus 100 for estimating body temperature includes a sensor 110 and a processor 120.

The sensor 110 may obtain spectra in two or more different light paths. The sensor 110 may include one or more light sources that emit light onto an object, and one or more detectors that detect light which returns after reacting with tissue of the object by being scattered or reflected from the object. In order to obtain spectra through the multiple different light paths, the sensor 110 may include a first combination of a single light source and a plurality of detectors that are disposed at different distances from the single light source, a second combination of a single detector and of a plurality of light sources that are disposed at different distances from the single detector, or a third combination of a plurality of light sources and a plurality of detectors that are disposed at different distances from the plurality of light sources. The light source may include a light emitting diode (LED), a laser diode (LD), a phosphor, etc., but is not limited thereto. Further, the detector may include a photo diode, a photo transistor, etc., or may be a spectrometer or a waveguide and the like connected to an external spectrometer. However, the detector is not limited thereto, and may include a complementary metal-oxide semiconductor (CMOS) image sensor, a charge-coupled device (CCD) image sensor, and the like.

The sensor 110 may include a light source array having light sources emitting light of different wavelengths to obtain spectra, and a single detector. In the case where a detector has a single photo diode as illustrated in FIG. 2A, light sources S1 and S2 may have a narrow light emission wavelength range (e.g., a light emission wavelength range less than a preset wavelength range) so as to split wavelengths, and the respective light sources S1 and S2 may have different light emission wavelength ranges which overlap a portion of a water absorption wavelength range. Alternatively, in order to obtain a spectrum, the sensor 110 may include one light source and one detector array, disposed at a distance from the light source, or a spectrometer connected to a light waveguide and the like. In this case, the detector array may have optical filters integrated therein and having different central wavelengths.

FIG. 2A illustrates an example of one detector D0 and two light sources S1 and S2 which are disposed at different distances from the detector D. In the example embodiment, the two light sources S1 and S2 are illustrated for convenience of explanation, but the number of light sources is not limited thereto. FIG. 2B illustrates an example of one light source 50 and two detectors D1 and D2 disposed at different distances from the light source 50. In this example embodiment, the number of detectors is not limited thereto. For convenience of explanation, the following description will be given with reference to the example of FIG. 2A.

Referring to FIG. 2A, the light sources S1 and S2 may emit light of different wavelengths. The wavelengths of the light sources S1 and S2 may include a wavelength range in which water absorption spectrum may be measured. The detector D0 may obtain an absorption spectrum by detecting light scattered or reflected from the object OBJ after the light is emitted by the light sources S1 and S2. For example, the detector D0 may detect a spectrum of a first light that travels in a first light path (hereinafter referred to as a "first spectrum") by detecting the first light that is scattered or reflected by a first tissue underneath the outer skin of the object after being emitted from the first light source S1 and then traveling to the first tissue. The first light path may start from the first light source S1, pass through the first tissue, and end at the detector D0. Further, the detector may detect a spectrum of a second light that travels in a second light path (hereinafter referred to as a "second spectrum") by detecting the second light that is scattered or reflected by a second tissue underneath the outer skin of the object after being emitted from the second light source S2 and then traveling to the second issue. In this case, at least one light path (e.g., the second light path) may pass through skin tissue located deeply below the surface of skin (e.g., dermis, or a tissue located at a position deeper than the dermis). For example, the first tissue may be an epidermis and the second tissue may be a dermis or a hypodermis which is located deeper than the epidermis. Alternatively, the first tissue may be a dermis and the second tissue may be a hypodermis.

In addition, To in FIGS. 2A and 2B denotes a reference temperature. Here, the reference temperature $T_0$ may refer to a surface temperature of the object. The surface temperature may be measured from the object using an external temperature sensor and the like, or may be a generally known surface temperature. However, the surface temperature is not limited thereto, and may be a pre-defined specific temperature, e.g., a general room temperature. $T_1$ denotes a mean temperature of the first light path (hereinafter referred to as a "first mean temperature"), and may be, for example, a mean temperature at a maximum penetration depth of the first light path. $T_2$ denotes a mean temperature of the second light path (hereinafter referred to as a "second mean temperature"), and may be, for example, a mean temperature at a maximum penetration depth of the second light path. Further, FIG. 2C illustrates a water absorption spectrum according to a temperature change. In this case, a spectrum measured in a water absorption wavelength range at the reference temperature $T_0$, or a spectrum obtained by converting a spectrum measured at a specific temperature to a spectrum corresponding to the reference temperature $T_0$, may be defined as a reference spectrum.

The first spectrum and the second spectrum, obtained by the sensor 110, may have different effective light path lengths and penetration depths, and may be expressed as a line integral for the effective light paths, as represented by the following Equation 1.

$$A_1(T) \sim \phi_0^{L_1} \varepsilon_w(T(s))ds \sim \varepsilon_{\mathit{eff},w}(T_0,T_1)L_1$$

$$A_2(T) \sim \phi_0^{L_2} \varepsilon_w(T(s))ds \sim \varepsilon_{\mathit{eff},w}(T_0,T_2)L_2 \quad \text{[Equation 1]}$$

Herein, $A_1(T)$ and $A_2(T)$ denote the first spectrum and the second spectrum measured by the sensor 110. $L_1$ denotes an effective light path between the first light source S1 and the detector D0, and $L_2$ denotes an effective light path between the second light source S2 and the detector D0. $T(s)$ denotes a temperature change function according to a position s in the light path; $\varepsilon_W(T(s))$ denotes an absorption coefficient per unit length of water, and a value which varies according to the temperature change T with a position s in the light path; $\varepsilon_{\mathit{eff},w}(T_0,T_1)$ denotes an effective absorption coefficient in the first light path; $\varepsilon_{\mathit{eff},w}(T_0,T_2)$ denotes an effective absorption coefficient in the second light path. $T_0$, $T_1$, and $T_2$ denote the reference temperature, the first mean temperature, and the second mean temperature, respectively; $(T_0, T_1)$ denotes a temperature interval from the reference temperature to the first mean temperature; and $(T_0, T_2)$ denotes a temperature interval from the reference temperature to the second mean temperature.

The processor 120 may estimate body temperature of the object by using the first spectrum and the second spectrum having different path lengths and obtained by the sensor 110.

For example, the processor 120 may normalize the first spectrum and the second spectrum obtained by the sensor 110. For example, the processor 120 may normalize a magnitude of the first spectrum and the second spectrum based on a light path of the reference spectrum. In this case, the processor 120 may normalize the magnitude of the first spectrum and the second spectrum by multiplying or dividing a pre-defined scaling factor. In addition, the processor 120 may obtain a pure water absorption spectrum by removing a substance (e.g., blood glucose, etc.) of the object from each spectrum. For example, an effect of a substance of the object may be removed by subtracting the substance of the object from each spectrum. In this case, a substance spectrum of the object may be a spectrum generally known for the substance, or may be a spectrum pre-obtained from a user by preprocessing.

The processor 120 may estimate a mean temperature for each path based on each of the normalized spectra and the reference spectrum, and may obtain a temperature slope that indicates a change of the estimated mean temperatures between the respective paths. Here, the temperature slope between the respective paths may refer to an effective temperature difference between the first mean temperature of the first path and the second mean temperature of the second path.

For example, the following Equation 2 is an example of a function for obtaining the first mean temperature of the first path by using the reference spectrum and the normalized first absorption spectrum. In this manner, the processor 120 may obtain the effective temperature difference, at which a curve of the first spectrum, measured in the temperature interval $(T_0, T_1)$ from the reference temperature $T_0$ to the first mean temperature $T_1$, may overlap the reference spectrum. By adding up the reference temperature $T_0$ and the effective temperature difference, the processor 120 may estimate the mean temperature $T_1$ of the first path.

$$\underset{\Delta T_1}{\text{minimize}} \left\| A_0(T_0) - \left(\overline{A_{1pw}(T)} + \Delta A_1\right) \right\| = \underset{\Delta T_1}{\text{minimize}} \left\| A_0(T_0) - \left(\overline{A_{1pw}(T)} + \frac{d\varepsilon_w}{dT}\Delta T_1\right) \right\|$$

[Equation 2]

Herein, $A_0(T_0)$ denotes the reference spectrum measured at the reference temperature $T_0$;

$$\overline{A_{1pw}(T)}$$

denotes the normalized first spectrum; $\Delta A_1$ denotes a difference between the reference spectrum and the normalized first spectrum;

$$\frac{d\varepsilon_w}{dT}$$

denotes a water absorption temperature coefficient, and may be a value pre-obtained by preprocessing; and $\Delta T_1$ denotes the effective temperature difference to be obtained for the first path. The mean temperature $T_1$ of the first path may be estimated by adding up the reference temperature $T_0$ and the effective temperature difference $\Delta T_1$. The difference $\Delta A_1$ between the reference spectrum and the normalized first spectrum may be converted into a relationship between the water absorption temperature coefficient $$\frac{d\varepsilon_w}{dT}$$

and the effective temperature difference $\Delta T_1$. A "minimize" function is a function for outputting the effective temperature difference $\Delta T_1$, at which a value of the function is minimized.

Likewise, by applying the above Equation 2, the processor 120 may obtain a mean temperature of the second path based on the reference spectrum and the normalized second spectrum. That is, the processor 120 may obtain the effective temperature difference, at which a curve of the second spectrum, measured in the temperature interval $(T_0, T_2)$ from the reference temperature $T_0$ to the second mean temperature $T_2$, may overlap the reference spectrum. By adding up the reference temperature $T_0$ and the effective temperature difference, the processor 120 may estimate the mean temperature $T_2$ of the second path.

The processor 120 may estimate a core body temperature $T_c$ of the object by using the obtained first mean temperature $T_1$, second mean temperature $T_2$, and reference temperature $T_0$. The core body temperature $T_c$ may refer to the temperature of the body's internal organs, and may be different from the reference temperature $T_0$ of the object which is measured from the skin surface. For example, the processor 120 may estimate the core body temperature $T_c$ of the object by using the following Equations 3 and 4.

$$T_c = T_s + K_g \cdot C \cdot (\Delta T_2 - \Delta T_1)$$ [Equation 3]

$$T_s = T_g + \Delta T_1$$ [Equation 4]

Herein, $T_c$ denotes the core body temperature of the object to be obtained; $K_g$ denotes a heat transfer coefficient of tissue of the object, and is a value pre-obtained by preprocessing; C denotes a calibration constant, and is a value pre-obtained by preprocessing; $\Delta T_1$ denotes the effective temperature difference of the first path; $\Delta T_2$ denotes the effective temperature difference of the second path, in which $\Delta T_2 - \Delta T_1$ denotes a temperature slope between the first path and the second path. $T_s$ denotes the mean temperature of the reference path, which may be any one of the first light path and the second light path. For example, the reference path may be the first light path which is the shortest path, in which the first mean temperature may be obtained by using Equation 4. For reference, the second mean temperature may be obtained by adding up the reference temperature and the effective temperature difference of the second path by using the above Equation 4.

In this embodiment, an accurate surface temperature of the object may not be known at the time of estimating the body temperature of the object, such that by estimating the body temperature based on a relative relationship between the first mean temperature at a position close to the surface and the second mean temperature at a relatively deep position, a change in environment factors affecting heat transfer, such as a change in external ambient temperature, humidity, air flow, and the like, may be minimized.

Figure 3:
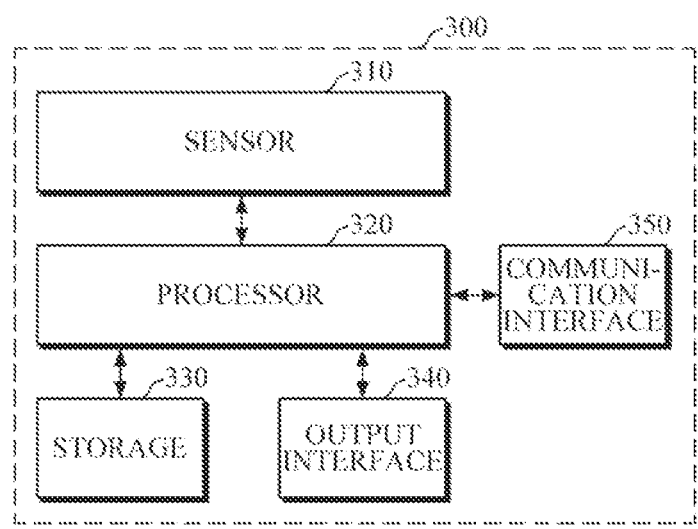
FIG. 3 is a block diagram illustrating an apparatus for estimating body temperature according to another example embodiment.

FIG. 3 is a block diagram illustrating an apparatus for estimating body temperature according to another example embodiment.

Referring to FIG. 3, the apparatus 300 for estimating a core body temperature includes a sensor 310, a processor 320, a storage 330, an output interface 340, and a communication interface 350. In this case, the sensor 310 and the processor 320 may have substantially the same structure as the sensor 110 and the processor 120 shown in FIG. 1, such that a detailed description thereof will be omitted.

The storage 330 may store information related to estimating body temperature. For example, the storage 330 may store spectra obtained by the sensor 310, processing results of the processor 320, e.g., the normalized spectra, the first mean temperature, the second mean temperature, and a final body temperature value. In addition, the storage 330 may store a body temperature estimation model, the reference temperature, the reference spectrum according to the reference temperature, user characteristic information, and the like. In this case, the user characteristic information may include a user's age, gender, health condition, and the like.

The storage 330 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 340 may provide the processing results of the processor 320 for a user. For example, the output interface 340 may display the mean temperature of each path, the estimated final temperature value, and the like on a display. In particular, if the estimated body temperature value falls outside a normal range, the output interface 340 may provide a user with warning information by changing color, line thickness, etc., or displaying the abnormal value along with a normal range, so that the user may easily recognize the abnormal value. Further, along with or without the visual output, the output interface 340 may provide the estimated body temperature value for the user in a non-visual manner by voice, vibrations, tactile sensation, and the like using an audio output module such as a speaker, or a haptic module and the like.

The communication interface 350 may communicate with an external device to transmit and receive various data, related to estimating body temperature, to and from the external device. In this case, the external device may include an information processing device such as a smartphone, a tablet PC, a desktop computer, a laptop computer, and the like. For example, the communication interface 350 may transmit a body temperature estimation result to the external device, such as a user's smartphone and the like, so that the user may manage and monitor the estimation result by using a device having a relatively high performance.

In this case, the communication interface 350 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 4:
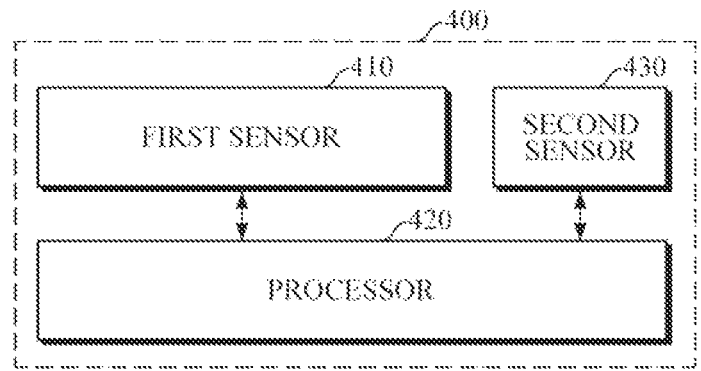
FIG. 4 is a block diagram illustrating an apparatus for estimating body temperature according to yet another example embodiment.
Figure 5:
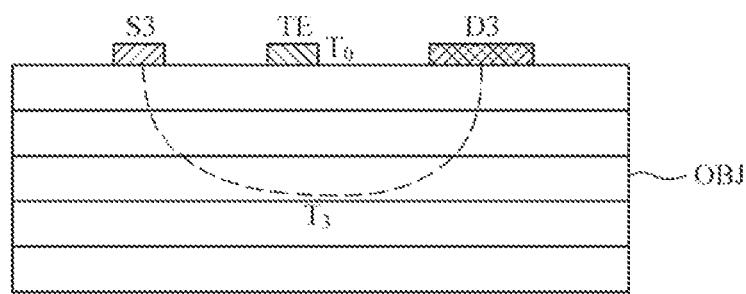
FIG. 5 is a diagram illustrating an example of a configuration of a sensor according to the example embodiment of the FIG. 4.

FIG. 4 is a block diagram illustrating an apparatus for estimating body temperature according to yet another example embodiment. FIG. 5 is a diagram illustrating an example of a configuration of a sensor according to the example embodiment of the FIG. 4.

Referring to FIG. 4, the apparatus 400 for estimating body temperature includes a first sensor 410, a processor 420, and a second sensor 430. In this case, the first sensor 410 and the processor 420 are the same as the sensor 110 and the processor 120 of the example embodiment of FIG. 1, such that the following description will be focused on non-overlapping parts. In addition, although not illustrated in FIG. 4, the apparatus 400 for estimating body temperature may include the storage 330, the output interface 340, and the communication interface 350 of FIG. 3.

Referring to FIG. 5, the first sensor 410 may include one light source S3 and one detector D3. In this case, a distance between the light source S3 and the detector D3 provides a light path penetrating into a skin depth, e.g., the dermis, or a deeper depth, at which temperature is to be estimated. However, the number of light sources and detectors is not limited thereto. The first sensor 410 may be implemented by a spectrometer.

The second sensor 430 may measure the surface temperature TO of the object while the first sensor 410 obtains a spectrum from the object OBJ. The second sensor 430 may be a contact temperature sensor, such as a resistance temperature detector, a thermocouple, a thermistor, or a thermistor. Alternatively, the second sensor 430 may be a non-contact temperature sensor, such as an infrared sensor. The second sensor 430 may be disposed between the light source S3 and the detector D3. However, the position of the temperature sensor is not particularly limited thereto.

The processor 420 may estimate body temperature of the object based on the spectrum obtained by the first sensor 410 and the surface temperature measured by the second sensor 430.

For example, as described above, the processor 420 may perform normalization based on the reference spectrum, pre-measured at the surface temperature in the water absorption wavelength range, or a spectrum obtained by converting a spectrum, measured from water or skin at a specific temperature, into a spectrum corresponding to the surface temperature; and may estimate the mean temperature of the light path based on the reference spectrum and the spectrum normalized by using the above Equation 2. Further, the processor 420 may obtain a temperature slope that indicates a change between the surface temperature and the estimated mean temperature of the light path.

The processor 420 may estimate a final body temperature value (e.g., a core body temperature value) by using the following Equation 5.

$$T_c = T_0 + K_g \cdot C \cdot \Delta T_s \qquad \text{[Equation 5]}$$

Herein, $T_c$ denotes a final body temperature value of the object to be obtained; $K_g$ denotes a heat transfer coefficient of tissue of the object, and is a value pre-obtained by preprocessing; C denotes a calibration constant, and is a value pre-obtained by preprocessing; $T_0$ denotes the surface temperature; and $\Delta T_s$ denotes the effective temperature difference between the surface temperature and the mean temperature of the light path, i.e., a temperature slope between the surface and the light path.

In this embodiment, an accurate surface temperature of the object may be known at the time of estimating body temperature of the object, such that by estimating a final body temperature value using the temperature slope between the surface temperature of the object and temperature at a relatively deep position, accuracy in estimating body temperature may be improved.

Figure 6:
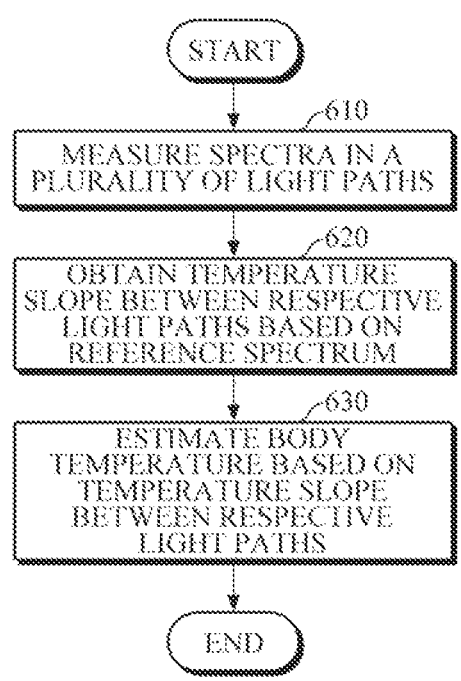
FIG. 6 is a flowchart illustrating a method of estimating body temperature according to an example embodiment.

FIG. 6 is a flowchart illustrating a method of estimating body temperature according to an example embodiment.

FIG. 6 is an example of a method of estimating body temperature which is performed by the apparatuses 100 and 300 for estimating body temperature according to the example embodiments of FIGS. 1 and 3, which are described above in detail, and thus will be briefly described below in order to avoid redundancy.

Referring to FIG. 6, the apparatus for estimating body temperature may measure a plurality of spectra in a plurality of different light paths of an object in 610. In this case, the plurality of light paths may include a path passing through a depth adjacent to the surface of the object, and a path passing through the dermis or a deeper position of the object.

Then, the apparatus for estimating body temperature may obtain a temperature slope for each path in 620 by using the spectra obtained for the respective paths in 610. As described above, the apparatus for estimating body temperature may estimate a mean temperature of each path based on the reference spectrum, the normalized first spectrum, and the normalized second spectrum by using the above Equation 2, and may obtain the temperature slope between the respective paths by using the mean temperature of each path.

Subsequently, the apparatus for estimating body temperature may estimate a final body temperature value based on the temperature slope between the respective paths in 630. The apparatus for estimating body temperature may estimate the body temperature of the object by using the temperature slope between the respective paths and the reference temperature.

Figure 7:
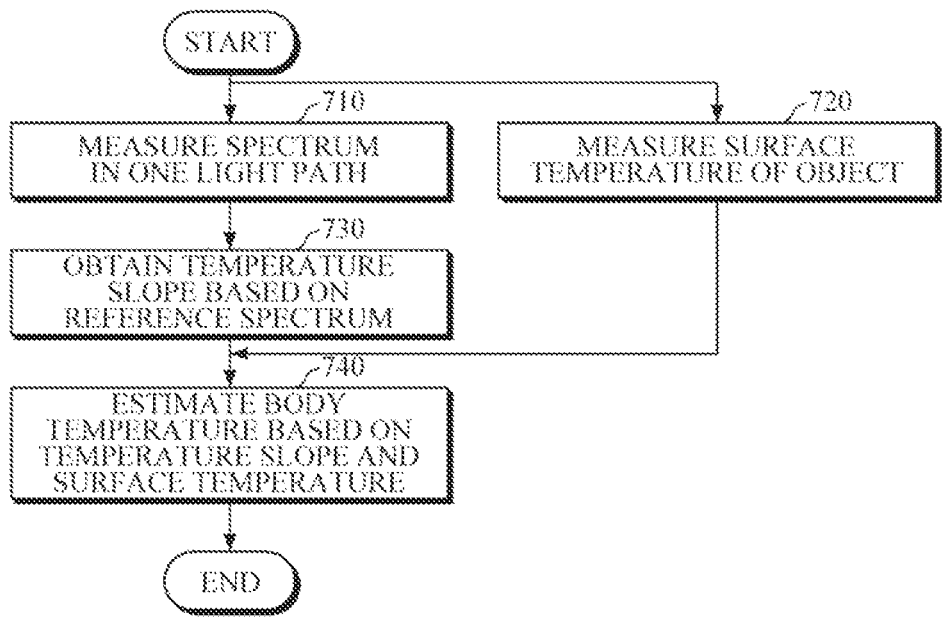
FIG. 7 is a flowchart illustrating a method of estimating body temperature according to another example embodiment.

FIG. 7 is a flowchart illustrating a method of estimating body temperature according to another example embodiment.

FIG. 7 is an example of a method of estimating body temperature that is performed by the apparatus 400 for estimating body temperature according to the example embodiment of FIG. 4, which will be briefly described below.

Referring to FIG. 7, the apparatus for estimating body temperature may first measure an absorption spectrum in one light path of the object in 710. In this case, the light path may include a path penetrating into a depth of the dermis or a deeper depth in the object.

Then, the apparatus for estimating body temperature may measure the surface temperature of the object during measurement of the spectrum from the object in 720.

Subsequently, the apparatus for estimating body temperature may obtain a temperature slope between the surface temperature and a mean temperature of the light path in 730 by using the reference spectrum and the spectrum obtained in 710.

Next, the apparatus for estimating body temperature may estimate a final body temperature value based on the temperature slope and the surface temperature in 740.

Figure 8A:
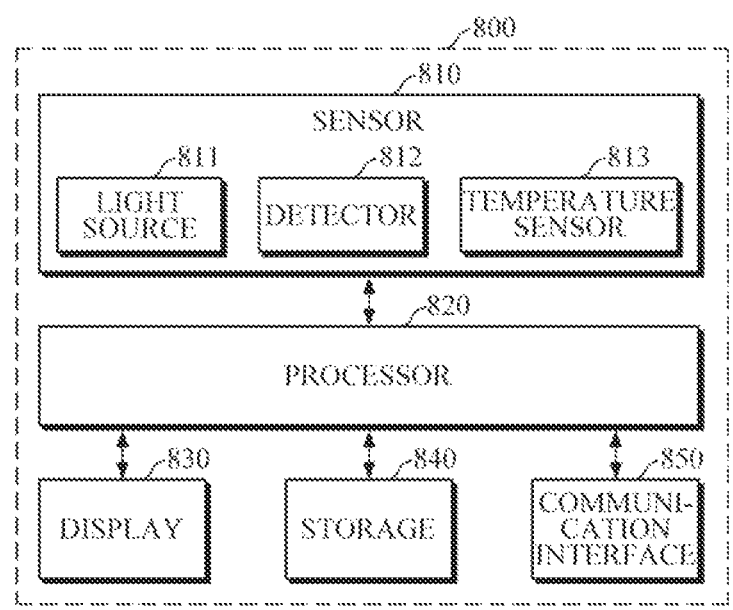
FIG. 8A is a block diagram illustrating a healthcare device according to an example embodiment.
Figure 8B:
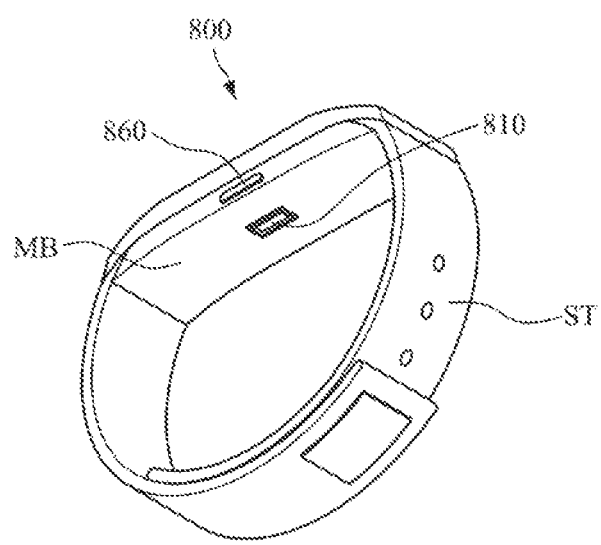
FIG. 8B is a diagram illustrating an example of a structure of a healthcare device.

FIG. 8A is a block diagram illustrating a healthcare device according to an example embodiment. The healthcare device 800 according to this embodiment may be manufactured as a separate device for measuring body temperature, or as an electronic device such as a smart watch, a smart band, smart glasses, smart earphones, a smart necklace, a smart ring, a smart patch, a smartphone, and the like. FIG. 8B is a diagram illustrating a smart watch, as an example of a structure of a healthcare device. However, the healthcare device is not limited thereto.

The healthcare device 800 according to this embodiment may include a function of estimating bio-information, as well as the aforementioned function of estimating body temperature. In this case, the bio-information may include triglyceride, body fat percentage, body water, blood glucose, cholesterol, carotenoid, protein, uric acid, blood pressure, vascular age, arterial stiffness, aortic pressure waveform, vascular compliance, stress index, fatigue level, skin age, skin elasticity, and the like.

Referring to FIGS. 8A and 8B, the healthcare device 800 in the form of a smart watch may include a main body MB and a strap ST.

The main body MB may be formed in various shapes, and a battery may be embedded in the main body MB and/or the strap ST to supply power to various components of the healthcare device 800. The strap ST may be flexible so as to be wrapped around a user's wrist. The strap ST may be composed of a first strap and a second strap which are separated from each other. One ends of the first strap and the second strap are connected to both sides of the main body MB, and the other ends thereof may be connected to each other via a connecting means. In this case, the connecting means may be formed as magnetic connection, Velcro connection, pin connection, and the like, but is not limited thereto. Further, the strap ST is not limited thereto, and may be integrally formed as a non-detachable band.

The main body MB may include various components. As illustrated in FIG. 8A, a sensor 810, a processor 820, a display 830, a storage 840, and a communication interface 850 may be mounted in the main body MB. However, depending on the size and shape of a form factor and the like, some of the display 830, the storage 840, and the communication interface 850, and a temperature sensor 813 may be omitted.

The sensor 810 may include two or more light sources 811 and at least one detector 812, or at least one light source 811 and two or more detectors 812, so as to have a plurality of different light paths. In addition, the sensor 810 may further include the temperature sensor 813 as illustrated herein, but the temperature sensor 813 may be omitted as needed. In the case where the sensor 810 includes the temperature sensor 813, the sensor 810 may include one light source 811 and one detector 812 so as to have one light path. The light source may include a light emitting diode (LED), a laser diode (LD), a phosphor, etc., but is not limited thereto. Further, the detector may include a photo diode, a photo transistor, and the like, or may include a spectrometer or a waveguide connected to an external spectrometer. However, the detector is not limited thereto, and may include a complementary metal-oxide semiconductor (CMOS) image sensor, a charge-coupled device (CCD) image sensor, and the like.

The sensor 810 may be disposed on a rear surface of the main body MB so as to come into contact with an upper portion of a user's wrist when the main body MB is worn on the user's wrist.

The processor 820 may be mounted in the main body MB and may be electrically connected to various components including the sensor 810. Upon receiving spectra of two or more different light paths from the sensor 810, the processor 820 may extract a reference temperature and a reference spectrum from the storage 840, and may estimate body temperature by using the plurality of spectra, the reference temperature, and the reference spectrum, as described above. In addition, upon receiving a spectrum of one light path and surface temperature from the sensor 810, the processor 820 may extract a reference spectrum, corresponding to the surface temperature, from the storage 840, and may estimate body temperature (e.g., core body temperature) by using the extracted surface temperature, the reference spectrum, and the spectrum of the light path.

In addition, the processor 820 may estimate bio-information by using an absorption spectrum received from the sensor 810. For example, the processor 820 may estimate bio-information by using a bio-information estimation model which defines a correlation between absorbance of the absorption spectrum and bio-information. In this case, the bio-information estimation model may be pre-obtained during preprocessing by training based on deep learning, artificial intelligence, and the like. Alternatively, the processor 820 may estimate, for example, blood glucose, from the absorption spectrum by using Net Analyte Signal (NAS) analysis and the like. In this case, the processor 820 may correct the bio-information estimation model based on the reference spectrum at the surface temperature. Alternatively, the processor 820 may obtain a scattering coefficient based on the absorption spectrum, and may estimate, for example, triglyceride, based on the obtained scattering coefficient. Various examples of estimating bio-information are described above, but the bio-information is not limited thereto and may be estimated based on the absorption spectrum by using various already known methods.

The processor 820 may selectively perform any one of two or more healthcare modes. For example, the processor 820 may perform a first mode of estimating body temperature, a second mode of estimating bio-information, and a third mode of estimating both body temperature and bio-information. In the third mode, the processor 820 may estimate body temperature and bio-information simultaneously or sequentially. Any one of the first, second, and third modes may be set as a default mode. The default mode may be changed by a user. In this case, information for setting the default mode may be stored in the storage 840. The processor 820 may estimate body temperature and/or bio-information by performing a mode according to a user's request input through the display 830, the manipulator 860, and other input means, or by performing the preset default mode stored in the storage 840.

The display 830 may be disposed on a front surface of the main body MB. The display 830 may include a display. In this case, the display may have a touch screen for receiving touch input. The display 830 may display a variety of functions performed by the processor 820, for example, guide information related to estimating body temperature and/or bio-information, and/or an estimation result.

The storage 840 may store a variety of information required for performing various functions of the healthcare device 800. For example, the storage 840 may include information related to estimating body temperature, such as the reference temperature, the reference spectrum, etc., information related to estimating bio-information such as a bio-information estimation model, etc., information related to user characteristics, and information such as an estimated body temperature value, an estimated bio-information value, and the like.

The communication interface 850 may communicate with an external device, such as a user's smartphone, to transmit estimation results of body temperature and/or bio-information, or to receive information such as a user's request input through the external device, the reference spectra measured at various reference temperature values, the bio-information estimation model, and the like.

The manipulator 860 may be formed on the crown of the side surface of the main body MB. The manipulator 860 may receive a user's command and may transmit the received command to the processor. In addition, the manipulator 860 may have a power button to turn on/off the wearable device 800.

While not restricted thereto, example embodiments can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating body temperature, the apparatus comprising:
a spectrometer comprising a detector and at least two light sources that are spaced apart from the detector by different distances, and configured to obtain a spectrum through a plurality of light paths between the at least two light sources and the detector through a tissue underneath a surface of an object;
a temperature sensor configured to measure a surface temperature from the surface of the object; and
a processor configured to:
determine temperature differences that minimize differences between the spectra of the plurality of light paths and a reference spectrum measured at the surface temperature, respectively,
obtain a temperature slope based on the temperature differences that minimize the differences between the spectra of the plurality of light paths and the reference spectrum; and
estimate the body temperature of the object based on the temperature slope.

2. The apparatus of claim 1, wherein the processor is further configured to normalize the spectra obtained through the plurality of light paths, based on the reference spectrum corresponding to the surface temperature, and obtain the temperature slope based on the normalized spectra.

3. The apparatus of claim 2, wherein the processor is further configured to estimate a mean temperature of each of the plurality of light paths, by adding the surface temperature to each of the temperature differences, and obtain the temperature slope based on the surface temperature and the mean temperature of each of the plurality of light paths.

4. The apparatus of claim 1, wherein the processor is further configured to estimate the body temperature of the object based on the surface temperature and the temperature slope by using a body temperature estimation equation.

* * * * *